United States Patent [19]

Hug

[11] 4,197,466
[45] Apr. 8, 1980

[54] GAS COMPRESSION INFRARED GENERATOR

[75] Inventor: William F. Hug, Pasadena, Calif.

[73] Assignee: The United States of America as represented by the Secretary of the Army, Washington, D.C.

[21] Appl. No.: 956,714

[22] Filed: Nov. 1, 1978

[51] Int. Cl.² ............................................. G01J 1/00
[52] U.S. Cl. .................................. 250/495; 250/493
[58] Field of Search ............... 250/493, 495, 494, 504; 315/111; 73/35

[56] References Cited

U.S. PATENT DOCUMENTS

| 3,751,666 | 8/1973 | Hug ........................................ 250/495 |
| 3,825,765 | 7/1974 | Anderson ................................ 250/495 |

OTHER PUBLICATIONS

"Optical Jammer Sources" Hug, Defense Documentation Center, Jun. 1973.

Primary Examiner—Bruce C. Anderson
Attorney, Agent, or Firm—Nathan Edelberg; Jeremiah G. Murray; Bernard Franz

[57] ABSTRACT

A molecular gas is compressed in a quasi-adiabatic manner to produce pulsed radiation during each compressor cycle when the pressure and temperature are sufficiently high, and part of the energy is recovered during the expansion phase, as defined in U.S. Pat. No. 3,751,666; characterized by use of a cylinder with a reciprocating piston as a compressor.

4 Claims, 10 Drawing Figures

380 cm³ COMPRESSOR 5 cm³ COMPRESSOR 43 cm³ COMPRESSOR 380 cm³ COMPRESSOR

SIDE VIEW OF 380-cm³ COMPRESSOR

GAS COMPRESSION INFRARED GENERATOR

The invention described herein may be manufactured and used by or for the Government for governmental purposes without the payment of any royalties thereon or therefor.

BACKGROUND OF THE INVENTION

This invention relates to infrared generators of the type in which a gas is heated by mechanical compression to a temperature sufficient for radiation.

Gas molecules can be excited at sufficiently high temperature and pressure so that energy of the molecules moves from the normal energy state to a state of higher energy. As the temperature increases, there is more collision between molecules and more molecules are raised to an energy state higher than ground state, thereby absorbing energy. The molecules return rather quickly to their lower energy state, and, in doing so, spontaneously emit electromagnetic radiation. The choice of gas will determine the fundamental vibrational wavelength band. The molecular species which are most applicable for use as infrared radiators in the 2 to 6 micron spectral region are listed in Table 1.

TABLE 1

| Molecule | Center Wavelength, microns |
|---|---|
| HF | 2.42 |
| HCl | 3.34 |
| CO | 4.60 |
| CN | 4.83 |
| NO | 5.25 |
| CO | 4.35 |
| $N_2O^2$ | 4.50 |

The fundamental concept for using molecular gases to provide efficient infrared radiation is that a gas layer is heated to a pressure and temperature sufficient to provide the optimum gas radiation in the fundamental molecular vibration band without exciting appreciably higher vibrational-rotational modes. This excitation of the gas molecules can be achieved by compressing the gas in a quasi-adiabatic manner (with substantially no change in heat energy) and with a resonantly driven gas compressor mechanism whereby at least some of the unradiated internal energy in the molecular gas, as well as some of the kinetic energy of the compressor mechanism during oscillation, can be recovered for further use during succeeding radiation pulses.

As shown in my U.S. Pat. No. 3,751,666, the compressor mechanism may be of the electromagnetic type including an armature connected to a diaphragm which forms a portion of the gas chamber and is driven by an armature current coil energized from a suitable current source for supplying the necessary magnetic field. Such a compressor mechanism has a much greater efficiency in infrared spectral bands than the usual arc discharge because a relatively small amount of radiation is lost at wavelengths outside the rotational-vibrational spectral band.

Ideally, a near adiabatic system is desirable; however, there are some thermal losses during compression owing to infrared radiation, and conduction losses from the compressed gas to the walls of the gas chamber.

The total internal energy of the gas at the peak of compression is equal to the product of the known mass of the molecular gas, the specific heat of the gas at constant volume (per unit mass) and the peak temperature which is related to the initial temperature by the compression ratio to the $-1$ power where is the specific heat ratio or the ratio of the specific heat at constant volume to the specific heat at constant pressure. When the gas compression member is released from its position at peak compression, the member will oscillate about the equilibrium position at a natural frequency determined by the mass of the number and the compression chamber design. The system energy during compression or expansion remains substantially constant and is equal to the sum of the gas energy and the kinetic energy of the compression member.

SUMMARY OF THE INVENTION

The object of the invention is to provide a highly efficient, modulatable source of infrared radiation in a given spectral band (specifically in the 4.0 to 5.5 micron spectral band).

The invention relates to an infrared generator using quasi-adiabetic periodic compression, as defined in the abstract and in claim 1 of my U.S. Pat. No. 3,751,666; characterized by the compression mechanism comprising a reciprocating piston in a cylinder.

DETAILED DESCRIPTION

Figure 1:
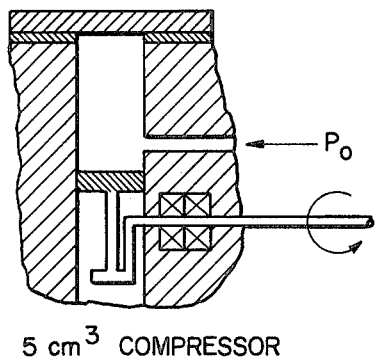
FIGS. 1, 2 and 3 are diagrams of three different embodiments of gas compressors used as infrared generators.

Earlier work on providing an infrared generator using compression of a molecular gas to a high pressure and temperature to provide pulsed radiation is covered by my U.S. Pat. No. 3,751,666. A continuation of this work is described in a Final Report by me on "Optical Jammer Sources" dated June 1973, cataloged by the Defense Documentation Center for limited distribution under the number AD 911075L. Copies of the patent and the report are enclosed with this patent application and made a part hereof by reference.

Spectral Efficiency and Radiance of Molecular Gases

The spectral distribution of the radiant output from any gas depends upon the temperature and pressure of the gas and the configuration of the radiating volume, i.e., its thickness and temperature and density gradients within it. At low temperatures a uniform slab of plasma will radiate principally resonance radiation. In the case of molecular gases the first vibration-rotation resonance band will be the predominant resonance radiation and the spectral output distribution or emissivity of the plasma slab has been calculated and/or measured for many molecular species.

The fundamental precept for using molecular gases to provide efficient radiation in select infrared spectral bands is that a gas layer is to be heated to a pressure and temperature sufficient to provide the optimum, unit emissive, gas radiance in the fundamental molecular vibration band without appreciably exciting higher vibrational-rotational modes. In order to obtain the desired infrared spectral efficiency we which to excite the fundamental vibrational-rotational transition ($i=1- -i=0$) with minimum excitation of higher states ($i=2, 3, 4, \ldots$). The spectral radiance of a molecular gas at any pressure and temperature can be determined from the spectral emissivity where the radiance is given by the product of the spectral emissivity and the Planck blackbody function. If the emissivity of the gas layer is unity everywhere within the spectral band of interest and zero at all other wavelengths, the spectral efficiency of the gas is 100 percent. Normally this is not the case. In the 4.0 to 5.5 spectral band of interest in a particular experimental project, carbon monoxide was selected for the best spectral efficiency.

General Compressor Efficiency Characteristics

In most types of radiation sources, spectral efficiency is a predominant portion of the overall source efficiency. In gas compression sources the predominant control of overall source efficiency is through the loss mechanisms involved with compressing the gas to the desired pressures and temperatures.

In an ideal lossless gas compressor a known mass of gas is compressed adiabatically. The total energy of the gas at the peak of the compression is defined by the product of the mass, specific heat at constant volume, and the peak temperature. When the piston is released from its position at peak compression, the potential energy stored in the compressed gas is translated into kinetic energy in the piston, connecting rods and flywheel. The system energy at any point during the compression or expansion constant as the sum of the gas energy and the kinetic energy of the mechanical components. Once this system is started it will continue indefinitely, transferring energy between the gas and the mechanism. If radiation from the gas were the only loss mechanism, the input power requirements would be only that required to make up for the energy lost by CO resonance radiation.

A further advantage of adiabatic gas compression heating is that the radiation is quenched during decompression not only by a decrease in temperatures, but also by the decrease in emissivity resulting from the decrease in pressure.

Since a large amount of energy must be invested in the gas to get it to this minimal radiating condition, small compression loss due to radiation, conduction, or gas leakage near the peak of compression can cause large losses in overall system efficiency. Compression losses decrease with increasing frequency such that an adiabatic compression condition is approached at high compressor frequencies.

The amount of energy lost from the compressed gas due to blow-by generally decreases with increasing frequency. The functional form of blow-by losses is very complicated partly because of the complex geometry of the blow-by annulus between the piston rings and cylinder wall and partly because the fluid dynamics problem is complicated by time and viscous effects. Simplifying the problem, the total mass of gas lost per compression cycle is limited first by flow choking effects due to the large pressure difference between compression chamber and crank case, and second by the decreasing amount of time available for mass loss at increased frequencies. An essential feature of blow-by is that the loss is a direct compression loss and thereby limits the peak temperatures, pressures, and also peak pulse radiant outputs achievable with the compressor. Fortunately, this loss diminishes with increasing frequency.

System Efficiency

The overall system efficiency does not necessarily depend on the compression efficiency of the source. Cylinder wall and bearing friction losses do not limit achievable compression pressures and temperatures, but do diminish the overall system efficiency. Energy loss from the compression volume due to blow-by can be reduced by compression ring and piston design, but in order to reduce blow-by, the frictional losses generally increase. The energy loss to the system due to friction between the piston rings and cylinder wall increases with frequency. Wall friction is generally independent of piston velocity and determined only by the tightness of the piston rings against the cylinder wall. The time averaged system power loss due to wall friction is therefore the product of the wall friction force (in the direction of piston motion) and the average piston velocity. The average piston velocity, on the other hand, is proportional to the product of the piston frequency and the total piston stroke distance.

The fricitonal loss due to bearings is also proportional to compressor frequency so that the input power to the system should generally change lineraly with frequency.

The time averaged radiant output power, on the other hand, should not change with frequency above frequencies where blow-by becomes negligible. At high frequencies the compression process is nearly adiabatic and the instantaneous pressure, temperature, and radiant output depend only upon the angular position of the crankshaft. For this case, the duty cycle of the output radiation is constant and the peak pulse radiant output is constant so that the time averaged radiant output is also constant.

System Trade-Offs and Limitations

The goal of the gas compression source design is to produce a device with maximum overall system efficiency and output for a given swept volume within the compressor. The swept volume of the compressor is a somewhat arbitrary constraint, but to a large extent the swept volume determines the overall system volume and power consumption. Within the constraint of fixed swept volume, the compression ratio and initial compression pressure and temperature are variable. It is with these variable parameters and the basic compressor mechanica˙ design that optimum efficiency is achievable.

There are two characteristic peak pressure-temperature regions of possible compressor operation; the optically thin and optically thick regions. These two regions are primarily defined in terms of the pressure-distance product of the compressed gas at the peak of compression.

At pressure-distance products below about 5 atm-cm, the compressed gas radiance due to fundamental resonance band radiation from CO is linear with pressure-distance product.

A major part of the problem is to adiabatically raise the gas temperature above 1500° K. At pressure-distance products above about 5 atm-cm. the compressed CO becomes increasingly opaque and the compressed gas radiance in the fundamental resonance band begins to approach blackbody conditions.

In either the transparent or blackbody emission limits it appears important to obtain the maximum peak compression temperature in order to achieve the greatest source output. In order to achieve the maximum compression temperature it is necessary to either increase the compression ratio, or the initial compression temperature. Of these choices, it appears best to increase the compression ratio since increased initial compression temperature decreases the percent modulation.

Let us consider factors which limit the compression ratio. A simple stress calculation puts a definite limit on the compression ratio obtainable with a device of the type comprising a piston moving in a cylinder. Bore, or piston diameter, is denoted by B, the stroke by S, the shaft diameter by $D_S$, the shaft length by $L_S$, and the piston thickness by $H_p$. The piston is supported by the connecting rod and crankshaft and during compression both support members experience compressive stress. This causes strain in the structure and prevents the piston from traveling the full distance, S. While this is not an important factor at compression ratios below 10:1, it becomes dominant at the levels being considered.

Operation of a compressor above the compression ratio limit is possible, but can only lead to increasing internal resonances within the compressor structure and ultimately the compressor destruction.

The optimization of a compressor of given size (or swept volume) depends upon the trade-offs between radiant output and compressor weight. Obviously, if weight were of no consideration, a compressor could be made sufficiently stiff as to withstand the considerable stresses necessary to achieve high peak compression temperatures at sufficiently high pressures to produce large unit emissive bandwidths in the output radiation.

A compressor of given mechanical construction has limited obtainable compression ratio determined by the structural limits of the design. The compression ratio limit is imposed by the peak compression pressure and the resulting elastic compression of the connecting rod and/or bending of the crankshaft. The surface radiance of compressed carbon monoxide can be calculated as a function of compression ratio for a compressor of given swept volume and given peak compression pressure.

Consider a 380 cm$^3$ compressor design to withstand a peak compression pressure of 1, 10, and 100 atm. Although the compressor designed to withstand only 1 atm peak pressure may be light weight, the maximum theoretical source surface radiance would only be about 0.1 W/cm$^2$ and this optimum will occur at the very low compression ratio of about 10. A heavier compressor, designed to withstand a peak pressure of 10 atm can produce an optimum theoretical source radiance about 0.4 W/cm$^2$ which occurs at an optimum compression ratio of about 40. The heaviest compressor considered here is designed to withstand a peak pressure of 100 atm, and can produce an optimum source radiance in excess of 100. For the 380 cm$^3$ compressor considered here, a peak compression pressure of 100 atm corresponds to a peak compression force of 9500 lb.

The overall system efficiency depends only in part on the peak radiant output of the device. The interrelationship between the peak radiant output and the power consumption factor will ultimately determine the overall source efficiency.

EXPERIMENTAL RESULTS

Three gas compression sources were evaluated. The first compressor had a stroke volume of 5 cubic cm, the second compressor was a 44 cubic cm device and the final device has a stroke volume of 380 cubic cm.

Five Cubic Centimeter Compressor

The earliest gas compression source data were obtained from the 5 cubic cm device basically described below and illustrated in FIG. 1.

Swept volume: 5.08 cubic cm;
Stroke: 1.39 cm;
Bore: 2.16 cm;
Piston area: 3.66 square cm;
T.D.C. gap: 1 mm (max);
Compression ratio: 200 (max).

The 5 cubic cm compressor used a cast aluminum piston sealed in the cylinder only by close tolerance fitting. Molybdenum disulfide was impregnated into the cast aluminum piston and into the main and connecting rod bearings for lubrication. This method of lubrication proved adequate for performing parametric tests although the lifetime of the device was very limited and the piston eventually froze in the cylinder. A significant amount of initial performance data was obtained with this device.

Forty-Three Cubic Centimeter Compressor

Figure 2:
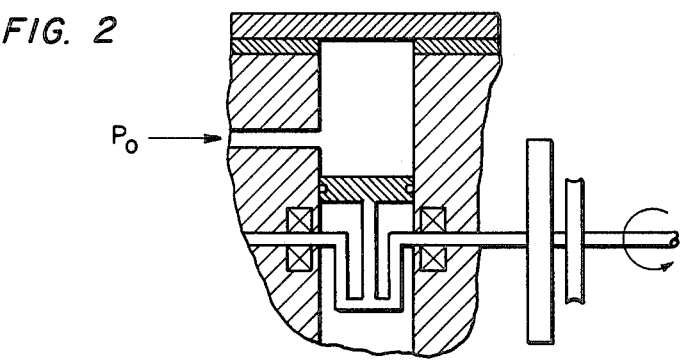
Figure 3:
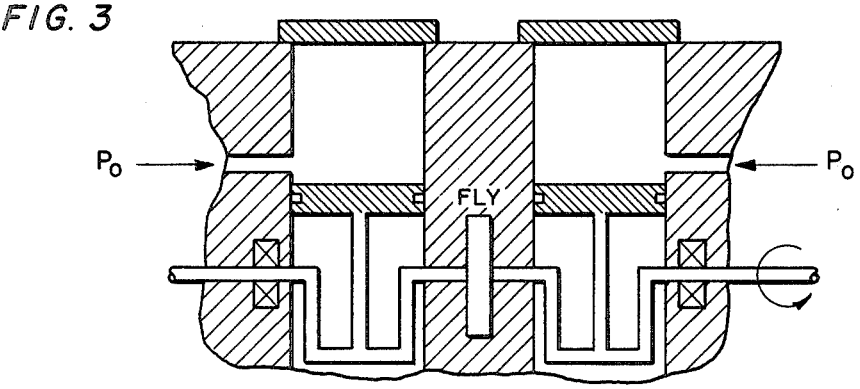

An assembled view of the 43 cubic cm device is shown in FIG. 2. Principal characteristics of the device are as follows:

Swept volume: 42.5 cubic cm;
Stroke: 2.03 cm;
Bore: 5.15 cm;
Radiating area: 20.85 square cm;
T.D.C. gap: 0.762 mm (nominal);
Compression ratio: 26.7:1 (nominal).

Most of the components in the cylinder assembly are cast or forged, heat-treated, aluminum. The crankshaft, with a throw of 1 cm, is symmetrically supported by roller bearings on either side of the connecting rod as illustrated in FIG. 2. A flywheel and pulley assembly were added to the crankshaft to reduce chatter in the assembly at high compression ratios. Both the crankpiston assembly and the flywheel were closely balanced and initial runs up to 72 Hz showed minor vibration in the compressor. Lubrication to the crankshaft, bearings, and cylinder walls is provided by a high pressure oiling system. A separate low capacity gear pump was used to provide oil at 75 psig.

During initial tests on the device the piston was sealed in the cylinder using rectangular spring action compression rings. Oil leakage from the crankcase into the compression volume during steady operation became a problem. Due to minimal oil leakage the sapphire compression volume window developed coatings sufficient to severely degrade the output radiation. The piston ring grooves were deepened and O-rings were inserted to both stiffen the compression rings and eliminate oil leakage around the back of the ring. This effectively eliminated the leakage problem with little apparent increase in the wall friction losses.

Three Hundred Eighty Cubic Centimeter Compressor

The basic specifications of the 380 cubic cm compressor are given below:
  Swept volume (total): 378 cubic cm;
  No. of cylinders: 2 (in phase);
  Chamber diam, B (each): 5.08 cm;
  Stroke, S (each): 8.90 cm;
  Compression ratio: 30:1 (nominal);
  Chamber depth in peak pulse: 3.06 mm.

Figure 4:
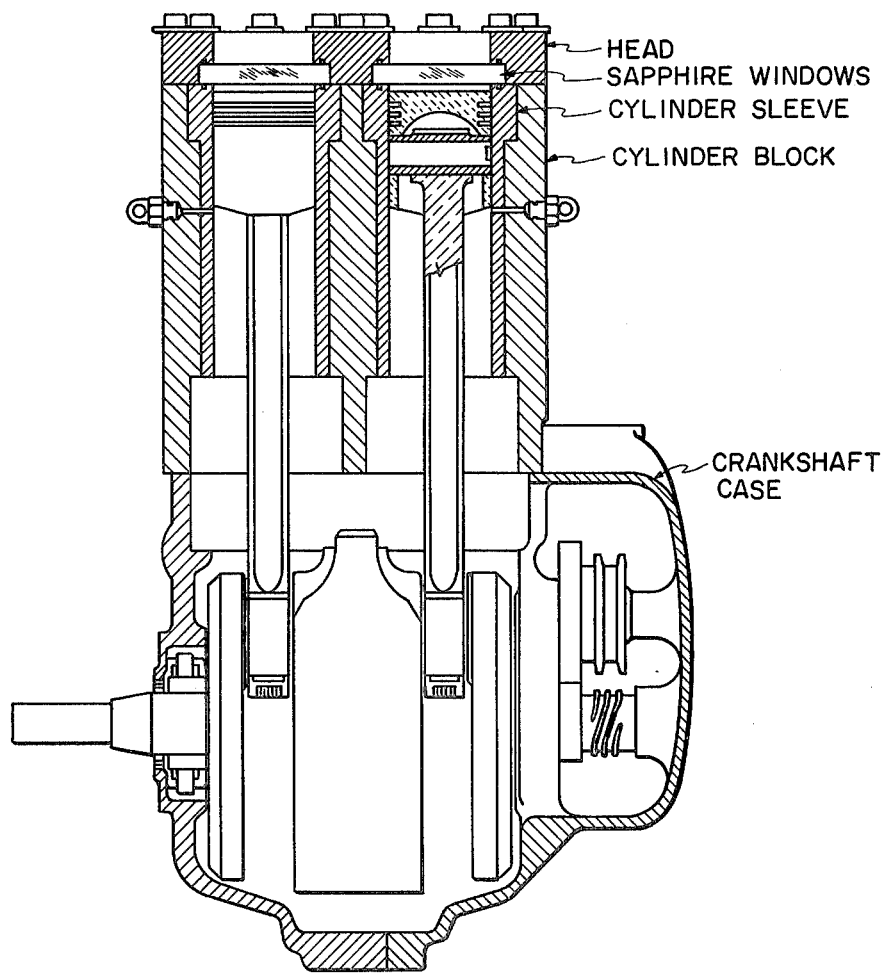
FIG. 4 is a sectional side view of the 380 cubic cm. compressor of FIG. 3.

A side view of the compressor is shown in cross-section in FIG. 4. The crankshaft housing is based on a Norton motorcycle crankcase modified for this compressor application. Significant changes were made in the base configuration to strengthen this structure to withstand peak compression forces in excess of 12,000 lb. Aluminum fillets and weldments were added prior to annealing and remachining of the crankcase. A special crankshaft was purchased with large radius fillets in the bearing support region to reduce stress concentrations in these regions. Additional weight was added to the internal flywheel to reduce peak load requirements on the driving motor.

Figure 5:
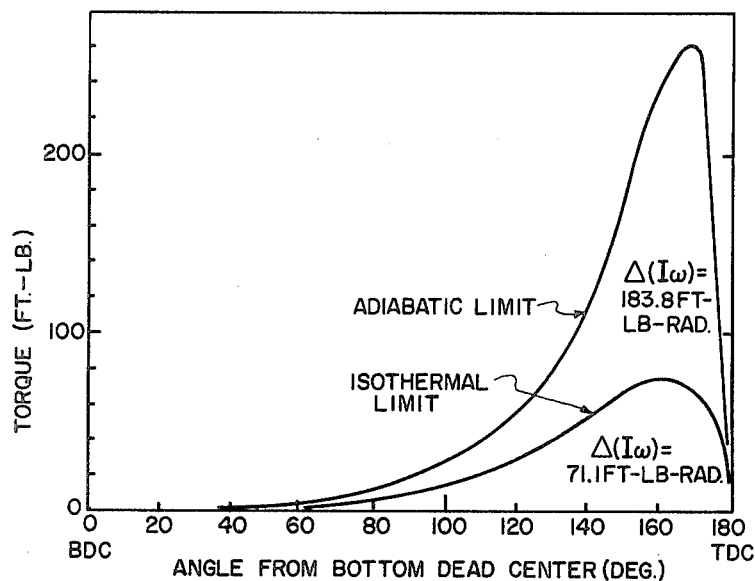
FIG. 5 is a graph showing the compression torque of the 380 cubic centimeter compressor.

The compression torque is shown in FIG. 5 as a function of angle from bottom dead center (BDC). The torque shown is based upon adiabatic and isothermal compression for a rod length of 22.85 cm, a compression ratio of 35:1, and an initial pressure of 1 atm, CO. During starting the compression frequency is low and the starting torque requirements are nearly represented by the isothermal compression torque limit. In the isothermal limit the total angular impulse due to one compression stroke is 71.1 ft-lb-radians, and in the adiabatic limit it is 183.3 ft-lb-radians. An external flywheel was added to the compressor so that at 1000 rpm the angular moment of inertial of the flywheel is ten times the adiabatic compression impulse.

The cylinder block was machined from a 2024 aluminum forging since no cast aluminum of comparable size could be purchased. Considerable difficulties were encountered is stress relieving this forging to obtain the precision tolerances.

The aluminum forging was initially annealed to relieve forging stresses before rough machining. The basic block configuration was then rough machined and then reannealed. A sequence of approximately six machining/annealing processes were undergone before the cylinder block was dimensionally stablized in its final configuration. The final dimensions of the cylinder block bore and the meehanite sleeve (FIG. 4) were determined such that the block would not separate from the sleeve up to temperatures near 400° K. Since meehanite has a much smaller coefficient of thermal expansion than aluminum, the sleeve will tend to separate from the aluminum block as the compresser temperature increases. The dimensionally stabilized aluminum block was bored to a diameter of 2.50000±0.0005 in. measured at room temperature. The outside diameter of the meehanite sleeve was chosen to give sufficient clearance to be pressed into the aluminum block with the block at room temperature and the sleeve at dry ice temperature. At room temperature the sleeve is thus in compression by the block providing good thermal contact and allowing friction heat from the cylinder to be dissipated. The outside diameter of the meehanite sleeve was thus machined to 2.5045±0.0005 in. at room temperature and the inside bore was rough cut slightly less than the desired 2.000 in. After this sleeve was pressed into the block, the final bore cut was completed.

The connecting rods were custom made to the required 22.85 cm length. These rods are of a configuration similar to those used in supercharged Offenhauser racing engines and are required to meet the severe peak compressive force loads.

The piston/ring assembly for the 380 cubic cm compressor was based on eliminating as much oil as possible from the compression area while maintaining adequate compression as well as maintaining a sufficient amount of oil on the cylinder walls to prevent piston seizure. The design consists of low expansion aluminum alloy pistons that have 0.006 cm skirt clearance that tapers to 0.010 cm clearance near the piston top. The oil control is provided by four independent ring assemblies that vary in individual oil handling capacity. The prime control is provided by the lowest oil ring that is located near the bottom edge of the piston skirt. This ring has a very high oil capacity and works in conjunction with a knife edge that is machined on the skirt edge. The ring consists of two high pressure steel rails separated by a cast iron insert which are all backed up by a spring steel expander. This ring is of the bottoming type that keeps the lower half of the piston centered in the cylinder bore. The next oil control ring is a scavenging type and is located just above the wrist pin. This ring is the type found in most four-cycle small bore engines and is non-bottoming and therefore is unaffected by any piston rocking. The ring is a one-piece cast iron type whose cross-section resembles a structural I-beam. The two uppermost rings are primarily there to maintain the pressure in the cylinder. There are standard tapered edge cast iron compression rings. The outer edge is unchromed to facilitate rapid break-in with minimal cylinder wear. The tapered edge provides a scrapping action to displace any remaining oil on the cylinder walls.

The spectral distribution of the radiant output and the peak pulse compressor radiance are parameters which deal principally with the compression efficiency on the success or failure of the compressor to achieve a near adiabatic radiating condition. If gas blow-by and/or heat loss from the compressed gas is negligible, the spectra and radiance of the compressed gas should closely approximate that predicted by the theoretical considerations given above.

Spectral output data from the 5 cubic cm molecular gas compressor was given in broad spectral band using an indium-antimonide detector, filtered using multilayer interference bandpass filters to view the spectral bands: 3.08 to 3.56 microns, 3.6 to 4.2 microns, 4.3 to 5.0 microns, and 5.0 to 5.5 microns. Using these spectral bandpass filters the output radiation in each band was analyzed and compared with that predicted theoretically. These data indicated the high potential spectral efficiencies possible from compressed carbon monoxide. In order to make a more detailed comparison of the theoretical emissivity model with the experimental data, additional spectral data using a Perkin-Elmer Model 112 monochromator were necessary.

Figure 6:
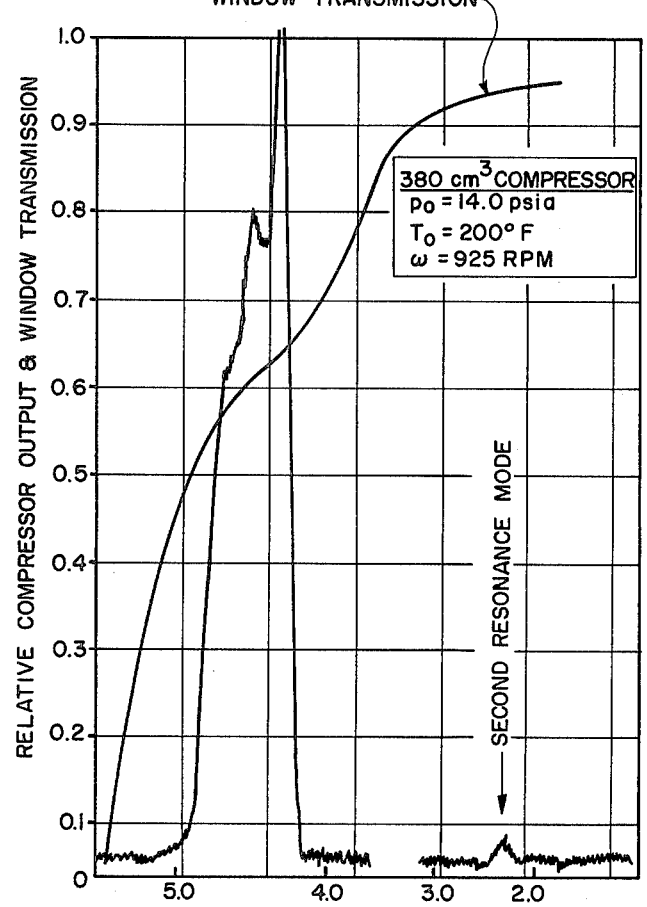
FIG. 6 is a graph showing the spectral output of the 380 cubic cm. compressor.

A spectral trace of the output radiation from the 380 cubic cm compressor was obtained. The spectral distribution shown in FIG. 6 covers the range from about 1.5 microns to 6.0 microns using a thermocouple detector in the monochrometer. The two principal features shown are the small second harmonic radiation at about 2.4 microns and the large increase in the peak compressor output to background radiation ratio. At the operating compression ratio of 30:1, the second harmonic generation indicated in FIG. 6 is the maximum expected from any of the data obtained.

Peak Pulse Compressor Radiance

The compressor radiance was inferred from measurements of the radiant intensity along a line normal to the compressed gas layer. Since the radiant output is essentially due to the fundamental vibration/rotation resonance band, the measurements were made with no bandpass limiting filters between the compressor and detector. The $LN_2$ cooled indium-antimonide radiometer used for these experiments was calibrated for responsivity at 4.7 microns using a 1000° C. blackbody standard of spectral irradiance and calibrated bandpass filters to limit the spectral bandpass of the known irradiation energy. Once the radiometer responsivity was known, the compressor radiance was computed.

This method of inferring the compressor output radiance assumes that the compressed gas layer radiates like a Lambertain source.

Figure 7:
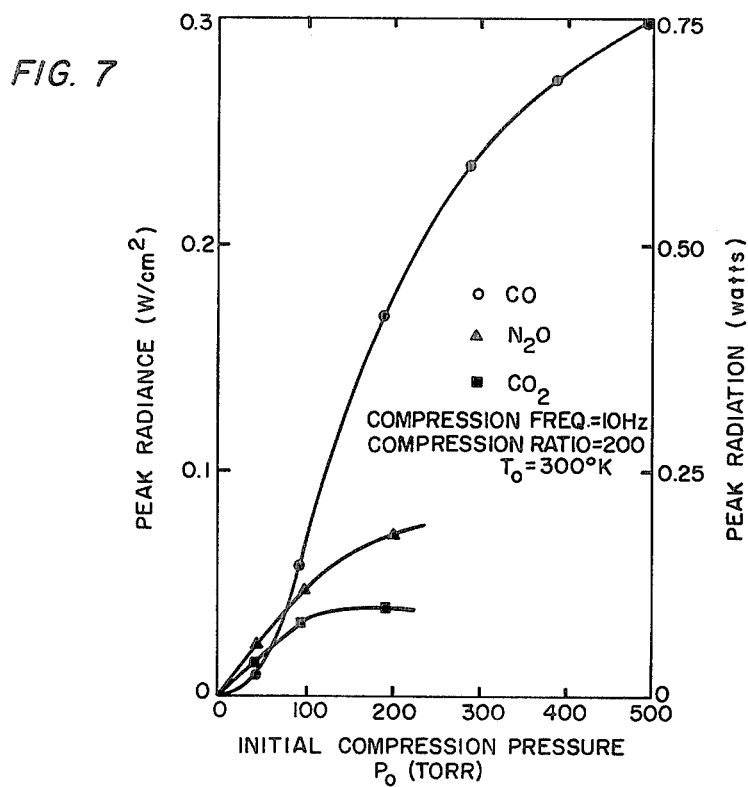
FIG. 7 is a graph showing the total spectral radiance of some molecular gases versus initial pressure at 10 hertz.

The comparative peak pulse compressor radiance values of a number of molecular gases has been found. For the sake of completeness the peak pulse radiance of the 5 cubic cm gas compressor is shown in FIG. 7 as a function of initial compression pressure for CO, $N_2O$, and $CO_2$. The obvious merits of CO both in peak pulse radiance as well as spectral match with the desired infrared band were thus shown.

Figure 8:
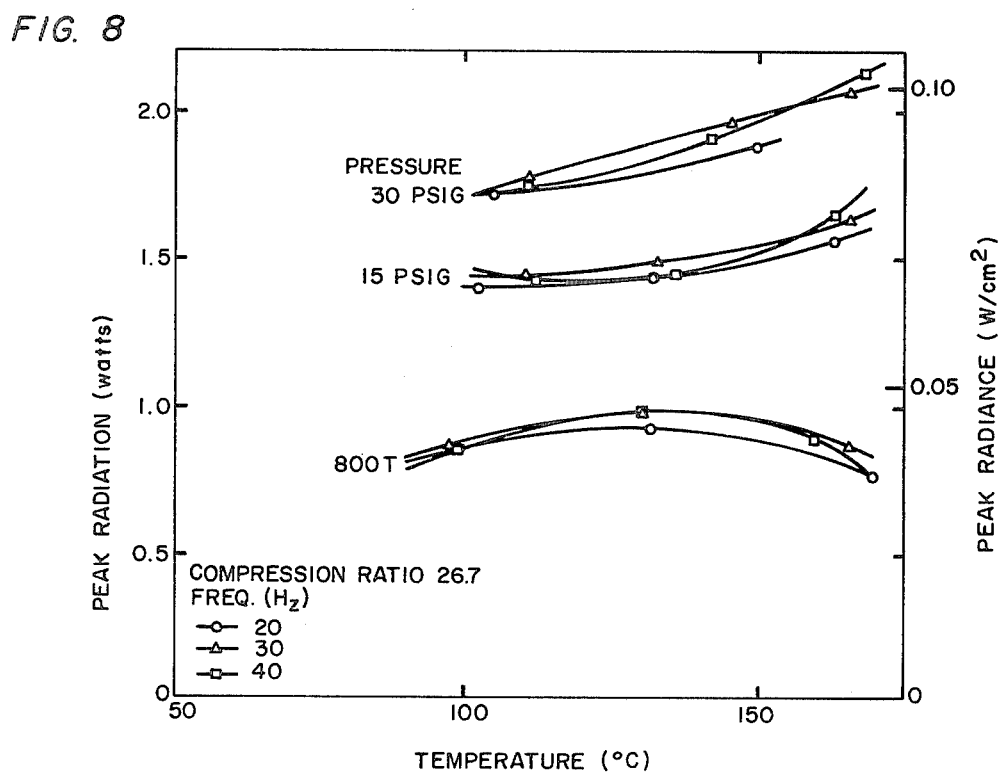
FIG. 8 is a graph for the 43 cubic cm. compressor showing the peak output and peak radiance as a function of initial compression temperature for three different initial compression pressures.

The peak output and source radiance of the 43 cubic cm compressor operated with CO as a working gas was measured as a function of initial compression pressure, initial compression temperature, and pulse frequency. FIG. 8 shows both the peak output and peak radiance as a function of initial compression temperature for three different initial compression pressures. Advantages gained in peak output due to increasing the initial temperature are not seen except at high initial compression pressures. In general, the effect is not strong over the range of temperatures investigated and the initial pressure is the more predominant factor. The influence of pulse frequency is also seen to be small. The initial compression temperature was predicted to have a greater influence on the compressor output than measured here. This anamolous result could be either a result of the temperature measurement method or increased compression losses at higher temperatures. The latter is not believed since at higher pressures the losses should be greater, not less, as shown by the output data. Variations in the initial temperature were provided by varying the entire compressor temperature using a thermal jacket surrounding the device. The initial compression temperature was assumed equal to the device temperature which may not have been accurate. The effect was nevertheless small.

The peak output and source radiance as were measured a function of the initial compression pressure with initial temperature and pulse frequency as parameters. Again, the effect of increased initial temperature is seen predominantly at the higher initial pressures. The strongest parameter is the initial pressure.

Figure 9:
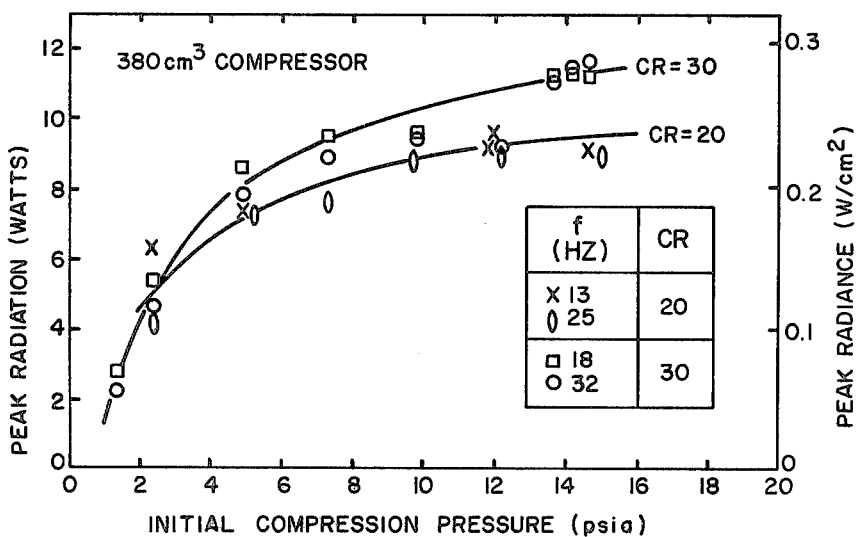
FIG. 9 is a graph of peak output and radiance of the 380 cubic cm. compressor.

The peak pulse output and source radiance of the 380 cubic cm compressor is shown in FIG. 9 as a function of initial compression pressure with compression ratio and pulse frequency as parameters. The effect of pulse frequency appears negligible in this plot, but the effect of compression ratio is distinguishable. No attempt was made during this series of tests to preheat the compressor since the influence shown for the 43 cubic cm compressor was so weak. The compressor operating temperature is solely due to frictional heating.

Comparison of Peak Compressor Outputs

The maximum output conditions achieved with any of the three compressors is shown below:

| Compressor | Peak pulse output (watt) | Peak pulse radiance (W/cm) |
| --- | --- | --- |
| 5 cm³ | 0.755 | 0.300 |
| 43 cm³ | 2.120 | 0.105 |
| 380 cm³ | 11.700 | 0.290 |

The maximum peak radiant output achieved with each of the three compressors is seen to be vastly different, but the peak radiance values are seen to be nearly the same. The peak output and radiance of the emitting gas layer is considerably greater than those listed above due to transmission losses in the sapphire windows used to seal the compression chamber. The 5 cubic cm and 43 cubic cm compressors used 6.25 mm thick windows while the 380 cubic cm compressor used 9.4 mm thick windows.

The 5 cubic cm compressor was operated at a theoretical compression ratio of 200:1 which was almost certainly never really achieved because of crankshaft deflection. The peak pulse radiance vs pressure curve for CO in FIG. 7 shows that the optimum blackbody radiating condition was never achieved in the 5 cubic cm compressor and that higher peak radiance and peak output values could have been achieved with this device at higher initial compression pressures. This compressor was not designed for these high peak pressures so that crankshaft defelction and associated high wear and short lifetime was experienced even at the maximum conditions for which the data is illustrated. At the highest pressures for which the device was operated severe pounding occurred and the piston eventually was frozen in the cylinder.

The 43 cubic cm compressor was never operated to the severe conditions of the 5 cubic cm device since longer lifetimes were needed to accumulate the large amount of data desired. The maximum peak pulse output and peak pulse radiance values achieved were consequently lower than the optimum achievable with the device. The limiting device pressure becomes quite obvious during operation since the noise level of the device sharply changed from a rather continuous to a pounding sound.

The 380 cubic cm compressor is by far the most rugged of the three compressors. As can be seen from FIG. 9, the peak pressures were elevated to well within the blackbody radiating condition of the compressed carbon monoxide resonance band without any noticeable pounding of the device. It is expected, therefore, that the compressor could be operated at high compression ratios and higher peak compression pressures. The 380 cubic cm compressor was designed to withstand 130 AFM peak pressures so that the maximum peak pulse radiance obtainable with the device should be between 0.5 and 1.0 $W/cm^2$ where the present window transmission is about 60 percent at 4.7 microns.

System Efficiency

Overall system efficiency data were obtained in the 43 cubic cm and 380 cm gas compressors. The system output energy per pulse was inferred from the system output intensity waveforms. The system output power (related to the output intensity) waveform can be integrated over a pulse to yield the output energy per pulse. The system efficiency can thus be calculated.

Figure 10:
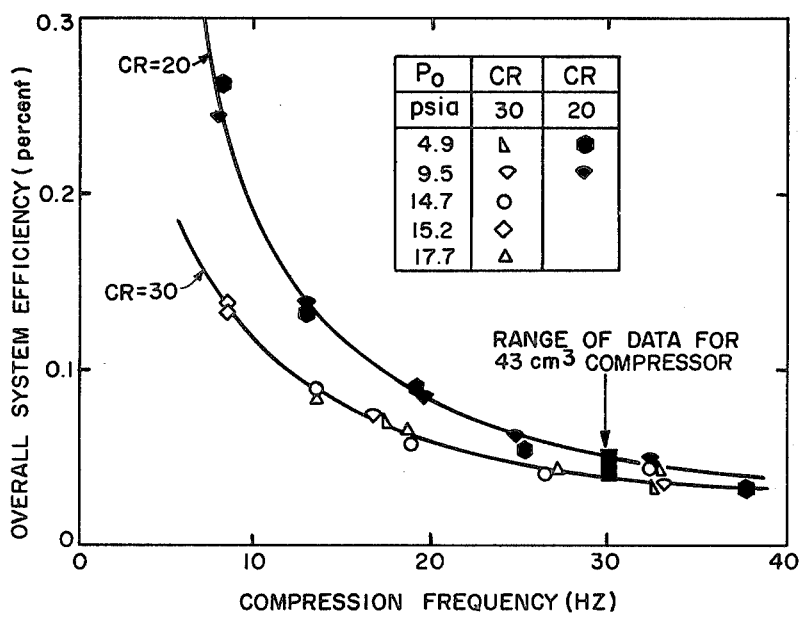
FIG. 10 is a graph showing effect of frequency on the 380 cubic cm. compressor efficiency.

The influence of pulse frequency on overall system efficiency is shown in FIG. 10 for the 380 cubic cm compressor and the range of 43 cubic cm system efficiency data at 30 Hz is also shown. The agreement between the optimum efficiency obtained with the 43 cubic cm system efficiency data at 30 Hz is also shown. The agreement between the optimum efficiency obtained with the 43 cubic cm system efficiency data at 30 Hz is also shown. The agreement between the optimum efficiency obtained with the 43 cubic cm and 380 cubic cm compressors is remarkable considering the significant differences between these two devices. The initial compression pressure is seen to offer little influence in the overall system efficiencies at pressures above about 5 psia. At lower pressures the peak pulse radiant output decreases as shown in FIG. 10 and the system efficiency decreases similarly. Although the peak pulse radiant output of the 380 cubic cm device is greater at CR=30 than at CR=20, the increase in the system power consumption is sufficiently greater to reduce the overall system efficiency at the increased compression ratio. The data are seen to describe a curve similar to that described theoretically. The efficiency at 100 Hz is 0.019 percent at CR=20.

RESULTS AND CONCLUSIONS

Peak Pulse Radiance

The range of peak pulse source radiance values achieved due to carbon monoxide resonance radiation are shown in FIG. 7 for the 5 cubic cm compressor, in FIG. 8 for the 43 cubic cm compressor, and in FIG. 9 for the 380 cubic cm compressor. All three compressors show a similar effect of increasing initial compression pressure and a nearly equal value of maximum measured source radiance. In each of these compressors the compression chamber was sealed with a flat sapphire window which was considerably thicker than required to maintain integrity. The measured source radiance values were therefore considerably smaller than potentially available with thinner windows.

The principal trade-off available in increasing the peak pulse source radiance is compressor rigidity and the resulting increase in system weight with increased rigidity. For the compressors tested on this program the maximum source radiance measured in the 4.0-5.5 micron band was about 0.30 W/cm$^2$. With thinner sapphire windows the maximum radiance may have been closer to 0.5 W/cm$^2$ which is in fair agreement with the theoretical results described in FIG. 13.

System Efficiency

The two efficiencies of interest here are the spectral and the overall system efficiency. FIG. 6 illustrates that the spectral efficiency of carbon monoxide compression sources is nearly 100 percent in the 4.0 to 5.5 micron spectral band.

The overall efficiency of the compression source systems was shown to depend inversely on pulse (or compression) frequency since the peak radiant output and radiation pulse duty cycle were nearly independent of frequency, but the power consumption is linearly proportional of frequency. The effect of pulse frequency on compressor efficiency is shown in FIG. 10 for the 380 cubic cm compression source. At 30 Hz both the 43 cubic cm and the 380 cubic cm devices produced the same overall system efficiency. This result is remarkable considering that the two compressors were of considerably different sizes and overall designs. Each source was independently optimized as much as possible to reduce bearing and cylinder friction and to minimize blow-by losses. The result of the two systems is, however, nearly identical in both peak pulse radiance and overall efficiency. It is therefore felt that the data are reasonably representative of the best achievable to date using a mechanical piston compressor to heat carbon monoxide to radiating conditions.

What is claimed is:

1. A pulsed infrared radiation source comprising an enclosed chamber having at least a portion thereof transparent to infrared radiation, said chamber containing a molecular gas having a fundamental vibrational wavelength band lying within the desired infrared radiation band and capable of emitting radiation within said infrared band when the pressure thereof exceeds a predetermined value, drive means for periodically compressing said gas with a very high compression ratio until the pressure exceeds said predetermined value, and the temperature rises by a nearly adiabatic process with the composition of said gas remaining fixed, said gas constituting a first energy storage means for storing energy between each period of compression, and second energy storage means to which is imparted during intervals between said periodic compression a substantial portion of the energy stored within said molecular gas;

the improvement wherein said chamber comprises a cylinder, and said drive means includes a piston which moves within the cylinder, with sealing means between the piston and cylinder to reduce the escape of said gas during compression to a very small amount.

2. An infrared radiation source according to claim 1, wherein said second energy storage means includes a flywheel mechanically coupled to said piston.

3. An infrared radiation source according to claim 2, including a second cylinder and piston, with both pistons having connecting rods to the same crankshaft, and the two pistons operated in phase.

4. An infrared source according to claims 1, 2 or 3, wherein a lubricant is supplied to the piston and cylinder outside the chamber; and wherein said sealing means comprises a first ring which has a very high lubricant capacity and works in conjunction with a knife edge that is machined on the skirt edge and comprises two high pressure steel rails separated by a cast iron insert which are all backed up by a spring steel expander, the first ring being of the bottoming type that keeps the lower half of the piston centered in the cylinder bore; a second ring for lubricant control of scavenging type located just above a wrist pin, the second ring being nonbottoming and therefore unaffected by any piston rocking and being a one-piece cast iron type whose cross-section resembles a structural I-beam; and second and third uppermost rings primarily to maintain the pressure in the cylinder, being standard tapered edge cast iron compression rings with the outer edge unchromed to facilitate rapid break-in with minimum cylinder wear, the tapered edge providing a scrapping action to displace any remaining lubricant on the cylinder wall.

* * * * *